United States Patent [19]
Irwin

[11] 3,949,613
[45] *Apr. 13, 1976

[54] LIQUID SAMPLING

[75] Inventor: Malcolm F. Irwin, West Chester, Pa.

[73] Assignee: Pro-Tech Inc., Malvern, Pa.

[*] Notice: The portion of the term of this patent subsequent to Mar. 11, 1992, has been disclaimed.

[22] Filed: Feb. 3, 1975

[21] Appl. No.: 546,346

Related U.S. Application Data

[62] Division of Ser. No. 412,275, Nov. 2, 1973, Pat. No. 3,869,921.

[52] U.S. Cl. ............................. 73/421 B; 417/145
[51] Int. Cl.[2] .......................................... G01N 1/14
[58] Field of Search .......... 73/421 B; 417/118, 120, 417/137, 143–147

[56] References Cited

UNITED STATES PATENTS

| 1,780,538 | 11/1930 | Redford et al. ..................... 137/102 |
| 3,751,983 | 8/1973 | Rutowski et al. ................. 73/421 B |
| 3,869,921 | 3/1975 | Irwin .............................. 73/421 B |

Primary Examiner—S. Clement Swisher
Attorney, Agent, or Firm—Charles A. McClure

[57] ABSTRACT

Successive samples are taken periodically from a body of liquid with the aid of pressurized fluid serving as both timing medium and sample propellant. The sampling apparatus is adjustable as to interval between successive samples, duration of taking of each sample, and sample lift.

5 Claims, 1 Drawing Figure

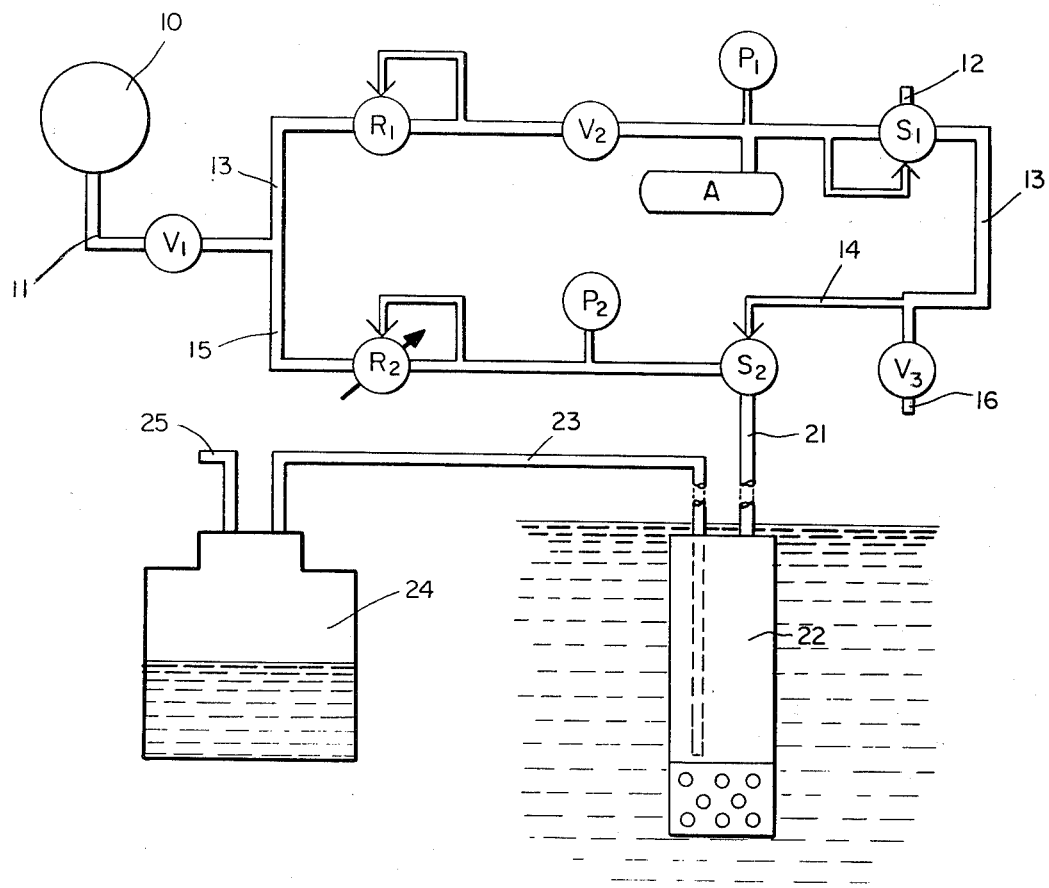

LIQUID SAMPLING

This is a division of application Ser. No. 412,275, filed Nov. 2, 1973, now U.S. Pat. No. 3,869,921.

LIQUID SAMPLING

This invention relates to sampling a liquid medium such as preliminary to determination of the composition thereof or of contaminants therein, concerning especially such sampling accomplished by use of a pressurized fluid for sample propulsion.

Manual techniques for sampling a medium for analysis or related purposes are giving way to automatic sampling, often electrically operated. Devices for setting frequency of sampling include spring-driven and electrical timing devices. Electrical operation is hazardous in an explosive atmosphere, such as may be encountered in oil refineries and other industrial operations, in sewers and sewage treatment plants, and in pollution-ridden areas. Electrical power lines are not available at remote sampling sites, and batteries often are cumbersome or otherwise unsatisfactory and require frequent replacement. Spring-winding is inconvenient, and spring motors are a source of maintenance requirements.

A primary object of the present invention is provision of a continuous-range adjustable high-to-low lift system for fluid-energized sampling of liquids.

Another object is flow-regulated control of sampling frequency and duration in such a system.

A further object is accomplishment of the foregoing objects by means of relatively simple apparatus.

Other objects of this invention, together with means and methods for attaining the various objects, will be apparent from the following description and the accompanying schematic drawing of a preferred embodiment thereof, which is presented by way of example rather than limitation.

In general, the objects of the present invention are accomplished with the aid of pressurized fluid serving as both timing medium and sample propellant. The apparatus of this invention is adjustable as to interval between successive samples and the duration of taking of each sample, by control of flow rates of the pressurized fluid, and is adjustable in sample lift by regulation of fluid pressure.

Source 10 of pressurized fluid connects via line 11, which conveniently contains on-off valve $V_1$, to two parallel branch lines, which may be viewed as low-pressure and high-pressure conduits, respectively.

First or low-pressure conduit 13 contains, in sequence, pressure regulator $R_1$, first flow-regulating valve $V_2$, pressure-responsive switching valve $S_1$, and finally second flow-regulating valve $V_3$, whose outlet 16 vents to the atmosphere. Accumulator tank A and low-pressure gauge $P_1$ are interconnected to the first conduit between the first flow-regulating valve and the pressure-responsive switching valve. The latter valve normally closes the conduit at its location but vents the downstream portion thereof via vent 12 thereof; it is responsive to the fluid pressure in the immediately upstream portion of the conduit, which interconnects directly to the accumulator tank and the pressure gauge, and opens at a predetermined pressure (simultaneously closing the vent) and recloses at a lower predetermined pressure.

Second or high-pressure conduit 15 contains adjustable pressure regulator $R_2$, which is normally set for a higher pressure than that for which low-pressure regulator $R_1$ in the first conduit is set. Pressure gauge $P_2$ is connected to the regulated downstream portion of this second conduit, which terminates in normally closed second pressure-responsive switching valve $S_2$ connected to sense and be responsive to (i.e., opened at a given level of) the pressure immediately upstream from valve $V_3$ in first conduit 13.

As shown connected for use, the outlet of switching valve $S_2$ is connected via line 21 to sample intake chamber 22 submerged in the body of liquid to be sampled. From the sample intake chamber, sample line 23 (with dip tube portion shown in broken lines inside the chamber) leads to sample collection container 24, which has vent tube 25 to the atmosphere.

Operation of the apparatus of this invention is readily understood by reference to the foregoing description and the accompanying illustration thereof.

With on-off valve $V_1$ in the on position, fluid under pressure from source 10 flows through line 11 into branch line 13, being the first or low-pressure conduit. Reduced to a predetermined pressure by pressure regulator $R_1$, the fluid flows on through the line at a rate determined by the setting of first flow-regulating valve $V_2$ and the pressure downstream therefrom, as indicated on low-pressure gauge $P_1$. The fluid collects at gradually increasing pressure, principally in accumulator tank A, until the switching pressure of normally closed first pressure-responsive switching valve $S_1$ is reached, whereupon the valve switches to the open position and releases the accumulated fluid to flow downstream and through second flow-regulating valve $V_3$ to the atmosphere at a rate controlled by the setting thereof. The surge of fluid into the part of branch conduit 13 located between the first switching valve and the second flow-regulating valve is sensed by sensing line 14 to normally closed second pressure-responsive switching valve $S_2$, which itself is located in second or high-pressure branch conduit 15. The resultant opening of the latter switching valve permits fluid to flow at such pressure, established by adjustable second pressure regulator $R_2$ and indicated on second pressure gauge $P_2$, into line 21 to sample intake chamber 22 submerged in the body of liquid to be sampled.

The sample chamber has a check valve (not shown) that enables liquid to enter the chamber, but when fluid under pressure is received via line 21 the check valve is forced shut and the liquid inside is propelled via line 23 therefrom into collection vessel or sample container 24, and propellant fluid is vented through vent 25 of the sample container. The flow of fluid at this relatively high pressure—as compared with the pressure in the other branch line—continues until second flow-regulating valve $V_3$ at the end of the low-pressure conduit has dropped the pressure therein sufficiently for first switching valve $S_1$ to reclose. Reduction of pressure in the accumulator tank to the reclosing level for first switching valve $S_1$ cuts off the supply of fluid into the terminal portion of the first conduit, and reclosing of $S_1$ also vents that terminal portion to the atmosphere through vent 12, thereby hastening the loss of pressure therein. Switching valve $S_2$—usually set to close below the reclosing pressure of $S_1$—then recloses, whereupon the system recycles. Thus, first flow-regulating valve $V_2$ mainly determines the interval between successive samples and second flow-regulating valve $V_3$ determines the duration of the time over which each sample is taken, which usually is much shorter than the period between successive samples.

The source of fluid under superatmospheric pressure may be located internal or external to the apparatus. The fluid source may comprise a reservoir of suitable fluid, such as nitrogen, helium, or other gaseous medium that is inert relative to the body of liquid and preferably also to any chemical tests to be performed upon the samples propelled thereby from the body of liquid. If air is not objectionable as a propellant, the source may be a tank of compressed air or a line from an air compressor wherever located.

Conventional materials of construction inert to the liquid being sampled are suitable for the various valves and other components. The flow-regulating valves, in addition to controlling the flow of fluid therethrough, may comprise visual indicators of flow rate, as by means of one or more balls or similar floats in a tapered tube as illustrated (e.g., FIG. 2) and described in U.S. Pat. No. 2,720,109. The pressure-responsive switching valves may be of the W-spring type shown (e.g., FIG. 5) and described in that patent or may be of the ball-controlled type shown (e.g., FIGS. 2a, 2b, 3a, 3b) and described in U.S. Pat. No. 3,751,983. The sample chamber conveniently is constructed as shown (FIGS. 6 and 5, respectively) and described in each of those patents.

By adjusting the setting of the pressure regulator for the high-pressure conduit the operator of this apparatus can adapt it readily to different lift requirements. Thus, for a 100 ft. deep well the source pressure (of perhaps 250 psi) may be dropped to about 50 psi. The pressure in the low-pressure line is conveniently reduced to about one atmosphere and the low-pressure switching valve set to open at about 16 psi and to reclose at about 14 psi, for example. The high-pressure switching valve may open at not so high a pressure (e.g., 15 psi) and reclose at a somewhat lower pressure (e.g., 5 or 10 psi). Alternatively, the respective switching valves could be set so that the band through which the low-pressure valve operates is broader than that through which the high-pressure valve operates (e.g., first valve to open at 25 psi and reclose at 10 psi, high-pressure valve to open at 20 psi and reclose at 15 psi) but this is not preferred because of the excessive venting of fluid by the timing circuitry and perhaps unduly short resulting sample duration.

Although only a single embodiment of this invention has been described and illustrated here, modifications may be made therein, as by adding, combining, or subdividing parts or steps, or by substituting equivalents, while retaining distinctive advantages and benefits of the present invention, which itself is defined in the following claims.

I claim:

1. In liquid sampling procedure operable from a source of propellant fluid under high pressure to collect samples of liquid from a body thereof, wherein such fluid is utilized as both a sample propellant and as a timing medium for controlling the interval of time between successive samples and the duration of time for collecting each sample, the improvement comprising establishing a low-pressure timing path from the fluid source to the atmosphere and establishing a high-pressure propulsion path from the fluid source to the body of liquid and on to a sample collection location, normally closing off the propulsion path to the body of liquid from the pressurized fluid source and opening such propulsion path intermittently at timed intervals to admit such fluid under relatively high pressure to propel a sample therefrom.

2. Liquid-sampling procedure according to claim 1, including preadjustably controlling the pressure in the high-pressure propulsion path and thereby determining the maximum lift of the sample.

3. Liquid-sampling procedure utilizing gaseous fluid from a source thereof under relatively high pressure, comprising establishing a normally closed propulsion path for such fluid from the source to a body of liquid to be sampled, establishing a timing path for such fluid from its source to the surrounding atmosphere and having its outlet end normally closed, reducing the fluid pressure at the inlet to the timing path to a value that is low relative to the source pressure but that is above atmospheric pressure, dividing the timing path into a first or fluid-accumulation part and a conjoined second or fluid-discharge part, controlling the flow of fluid continuously from the source into the first part of the timing path for accumulation therein at a pressure gradually rising toward such value, controlling the flow of such accumulated fluid from the first part to the second part of the timing path by normally closing off their junction but opening it intermittently whenever the accumulating fluid reaches a preselected pressure level, simultaneously opening the propulsion path and displacing a sample of liquid with the resulting flow of fluid from the source, thereby controlling the interval between successive samplings, also controlling the outflow of such fluid from the second part of the timing path to the atmosphere at a preselected rate, and reclosing the junction between the first and second parts of that path when the fluid pressure therein falls to a preselected lower value and simultaneously reclosing the propulsion path to discontinue the flow of fluid therethrough.

4. Liquid-sampling procedure according to claim 3, including regulating the fluid pressure in the propulsion path to a value below the source pressure but above the pressure in the timing path.

5. Liquid-sampling procedure according to claim 4, wherein the regulated pressure is preselected to provide a desired maximum sample lift.

* * * * *